United States Patent
Zhang et al.

(10) Patent No.: US 9,683,070 B2
(45) Date of Patent: Jun. 20, 2017

(54) BIO-BASED SUPERABSORBENTS PREPARED VIA THE MACROMONOMER APPROACH

(71) Applicant: WASHINGTON STATE UNIVERSITY, Pullman, WA (US)

(72) Inventors: Jinwen Zhang, Pullman, WA (US); Wenjia Song, Pullman, WA (US)

(73) Assignee: Washington State University, Pullman, WA (US)

(*) Notice: Subject to any disclaimer, the term of this patent is extended or adjusted under 35 U.S.C. 154(b) by 0 days.

(21) Appl. No.: 15/340,213

(22) Filed: Nov. 1, 2016

(65) Prior Publication Data

US 2017/0044294 A1 Feb. 16, 2017

Related U.S. Application Data

(62) Division of application No. 14/705,385, filed on May 6, 2015, now Pat. No. 9,511,168.

(60) Provisional application No. 61/994,046, filed on May 15, 2014.

(51) Int. Cl.
| | |
|---|---|
| C08F 2/00 | (2006.01) |
| C08H 1/00 | (2006.01) |
| C08F 290/08 | (2006.01) |
| A61L 15/24 | (2006.01) |
| A61L 15/60 | (2006.01) |
| A61L 15/62 | (2006.01) |

(52) U.S. Cl.
CPC ............ *C08F 290/08* (2013.01); *A61L 15/24* (2013.01); *A61L 15/60* (2013.01); *A61L 15/62* (2013.01)

(58) Field of Classification Search
CPC ........ C08F 290/08; A61L 15/62; A61L 15/60; A61L 15/32
USPC .............................. 526/199, 238.1
See application file for complete search history.

(56) References Cited

U.S. PATENT DOCUMENTS 6,565,842 B1 * 5/2003 Sojomihardjo ...... A61K 9/1652
424/178.1

* cited by examiner

*Primary Examiner* — William Cheung
(74) *Attorney, Agent, or Firm* — Whitham, Curtis & Cook, P.C.

(57) ABSTRACT

A novel bio-based superabsorbent polymer material based on a proteinaceous natural polymer is introduced herein. There is further disclosed a method for the manufacture of such a bio-based crosslinked superabsorbent polymer material. The method includes, but not limited to, introducing polymerizable unsaturated groups onto the natural polymer or its derivative so as to yield a macromonomer. The macromonomer can be formed by covalently binding unsaturated carbon-carbon double bonds to a proteinaceous substrate through a reaction of a selected chemical compound and the amino group on the proteinaceous substrate. The macromonomer is then copolymerized with unsaturated co-monomer(s) to form a crosslinked superabsorbent material.

8 Claims, 1 Drawing Sheet

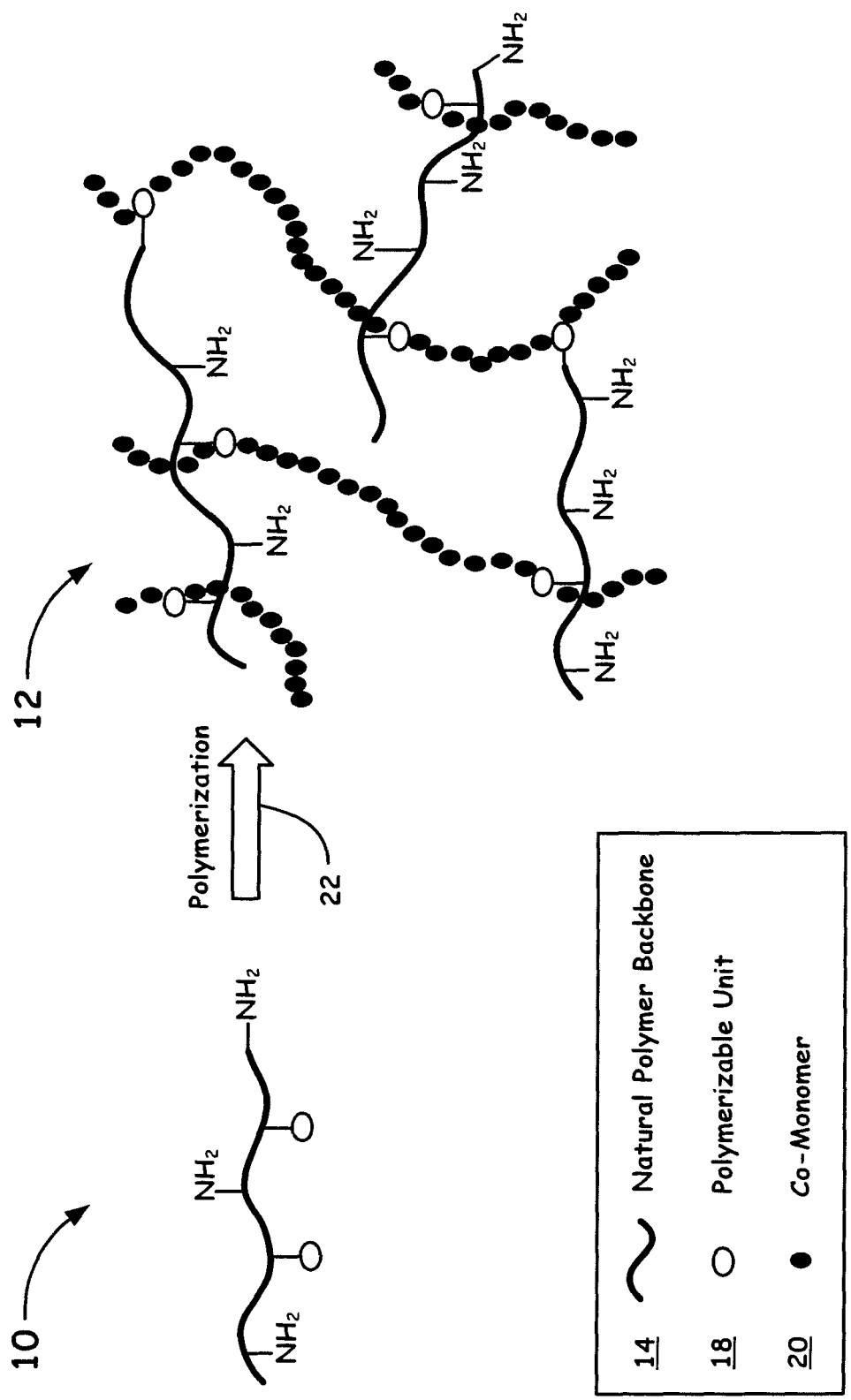

BIO-BASED SUPERABSORBENTS PREPARED VIA THE MACROMONOMER APPROACH

CROSS-REFERENCE TO RELATED APPLICATIONS

This application is a Divisional Application of U.S. Ser. No. 14/705,385, filed May 6, 2015, now U.S. Pat. No. 9,511,168. The present application claims under 35 U.S.C. §119, the priority benefit of U.S. Provisional Application No. 61/994,046, filed May 15, 2014, entitled: "BIO-BASED SUPERABSORBENTS PREPARED VIA MACROMONOMER APPROACH", now issued as U.S. Pat. No. 9,511,168. The disclosure of the foregoing application is incorporated herein by reference in its entirety.

BACKGROUND OF THE INVENTION

Field of the Invention

The embodiments of the present invention relate generally to bio-based superabsorbent polymer materials based on renewable, natural polymers. More specifically, the embodiments disclosed herein relate to a cross-linked superabsorbent polymer material derived from natural polymers that includes proteinaceous substrates and having superabsorbent properties in aqueous fluids, and a method to produce such a crosslinked superabsorbent polymer material.

Discussion of the Related Art

A superabsorbent polymer is a crosslinked polymer network that is capable of absorbing and retaining an extraordinary amount of water (10~1000 times its own weight). The thermodynamic mechanism of a superabsorbent polymer requires the polymer network to have sufficient numbers of hydrophilic, especially ionic groups. The hydrophilicity of these groups drives the superabsorbent polymer to absorb and retain large amounts of water or aqueous fluids. Crosslinking is necessary to prevent the polymer from dissolving in water and allow structural integrity of the superabsorbent material. The ionic content and crosslinking degree of the polymer network determine the properties of the superabsorbent material such as degree of swelling of the superabsorbent hydrogel, mechanical strength and water retention capacity.

Conventional superabsorbent polymer by volume of production according to the state of the art is polyacrylic acid-based, which often includes sodium salts of polyacrylic acid and a copolymer of acrylamide and acrylic acid. Polyacrylic acid itself is synthesized through free radical polymerization of acrylic acid, a monomer predominately derived from oxidation of propylene. Crosslinking of polyacrylic acid-based polymers is usually provided by a chemical compound called crosslinking agent that contains at least two unsaturated carbon-carbon double bonds. Superabsorbent polymers are used for applications such as baby diapers and adult hygiene products, soil additives, water purification, oil treatment, and industrial dewatering. Growing demand of superabsorbent polymer materials and increasing oil price strongly motivates the utilization of bio-based alternatives to current superabsorbent materials.

Background information on a protein-based natural polymer to make superabsorbent polymers is described and claimed in U.S. Pat. No. 8,148,501, entitled, "ABSORBENT PROTEIN MEAL BASE HYDROGELS," issued Apr. 3, 2012, to Benecke et al., including the following, "absorbent hydrogels are formed by reacting a protein meal base, a radical initiator and a polymerizable monomer. Optionally, a cross-linking agent and/or a radical accelerant, such as tetramethylethylenediamine (TMEDA) or sodium bisulfite (NaHSO$_3$), is also added to the mixture. Preferably, the radical initiator is ammonium persulfate (APS) or potassium persulfate (KPS), and the cross-linking agent is preferably trifunctional trimethylolpropane trimethacrylate (TMPTMA) or methylene bisacrylamide (MBA). The polymerizable monomer is preferably acrylic acid, or a combination of acrylic acid and acrylamide."

Background information on a superabsorbent biodegradable hydrogel based on acylated-protein but substantially free of residual cross-linkers is described and claimed in U.S. Pat. No. 6,310,105, entitled, "CARBOXYL-MODIFIED SUPERABSORBENT PROTEIN HYDROGEL," issued Oct. 30, 2001, to Damadoran, including the following, "the present invention is a biodegradable, reversibly-swellable, polyvalent cation-binding, protein hydrogel which comprises an acylated protein matrix in which the acylated protein matrix is crosslinked with a bifunctional crosslinking reagent, and treated with a polar organic solvent, and a method of making the same."

Background information on a manufacturing methodology of a superabsorbent polymer based on modified polysaccharides is described in U. S. Application No. 2013/0338354, entitled, "RENEWABLE SUPERABSORBENTS," published Dec. 19, 2013, to Albertsson et al., including the following, " . . . the present invention relates to a crosslinked polymer material derived from hydrolysates comprising hemicelluloses and having superabsorbent properties in water based fluids, and a method to produce such a crosslinked polymer material."

The above cited art, while respectively beneficial, nonetheless have drawbacks that are addressed by the teachings herein. For example, the renewable content in the above cited art is usually low when beneficial high water absorbency is achieved. It is also to be noted that the mechanical strength of the hydrogel is often compromised due to the way the natural polymer and synthetic component of the desired superabsorbent hydrogel is assembled. In addition, chemical modifications of polysaccharides, such as in U. S. Application No. 2013/0338354, involve expensive chemicals and/or processes. Moreover, while the method based on the modified polysaccharides through hydroxyl groups lends itself to a superabsorbent material, the reactivity of the hydroxyl groups contained in the polysaccharides is less than desirable.

Accordingly, there is a need in the art for an improved method of manufacturing bio-based superabsorbent polymer materials through an approach of macromonomer derived from natural proteinaceous polymer(s). The embodiments disclosed herein address such a need.

SUMMARY OF THE INVENTION

The present application is directed to a novel bio-based superabsorbent polymer material as well as the method of producing such a material based on a macromonomer derived from natural proteinaceous polymer.

An aspect of the present application is directed to method of manufacturing a polymer material that includes providing a natural polymer substrate including at least one protein; modifying at least part of the protein by covalently bonding polymerizable groups onto its structure through at least a portion of its amino groups using at least one polymerizable group-bearing compound; and co-polymerizing the modified substrate with one or more comonomer(s) to produce a crosslinked polymer material. That is, one or more of the amino groups of the protein are covalently bonded to a polymerizable group. The polymerizable group can be the same or different at the amino groups where covalent bonding occurs. One or more co-monomers, which can be the same or different from each other, are polymerized with the modified substrate, and form polymer chains extending from the covalently bound polymerizable group(s). The polymer chains formed from the co-monomers may extend between polymerizable group(s) on the same polymer chain of the modified natural polymer substrate or between polymerizable group(s) on different polymer chains of the modified natural polymer substrate, thereby crosslinking the chains. In some embodiments, crosslinking may also occur between the polymer chains formed from the co-monomers.

Another aspect of the present application is directed to a crosslinked superabsorbent polymer material that comprises at least a chemically modified proteinaceous natural polymer, wherein at least one proteinaceous natural polymer is modified by covalently bonding polymerizable groups onto its structure through at least part of its amino groups.

Accordingly, the present invention provides for a new bio-based superabsorbent polymer material and a method of making such a bio-based superabsorbent polymer material based on a proteinaceous natural polymer.

BRIEF DESCRIPTION OF THE DRAWINGS

FIG. 1 shows an example macromonomer methodology to provide for a novel bio-based superabsorbent material, as disclosed herein.

DETAILED DESCRIPTION

In the description of the invention herein, it is understood that a word appearing in the singular encompasses its plural counterpart, and a word appearing in the plural encompasses its singular counterpart, unless implicitly or explicitly understood or stated otherwise. Moreover, the terms used herein unless otherwise specified have the meanings commonly understood by those skilled in the art. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the FIGURE(s), as shown herein, are not necessarily drawn to scale, wherein some of the elements may be drawn merely for clarity of the invention.

Additionally, it is to be understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

It is also to be appreciated that the term "superabsorbent material," refers to a material that can absorb and retain large relative amounts of a liquid(s). Such superabsorbent materials have a swelling ratio (Q), as to be discussed herein, that is defined by a figure of merit from about 10 to about several hundred or more. The superabsorbent material does not dissolve in the liquid as enabled by a cross-linked network of the hydrophilic polymer. In turn, the material beneficially and in a novel fashion provides liquids to be absorbed so as to instead cause the structure of the material to swell, leading to an increase in volume.

It is also to be understood that the term "natural proteinaceous polymer" refers to any natural polymer that contains at least a portion of proteins with the rest being other naturally occurring polymers. Such natural proteinaceous polymer contains at least some amino groups based on which the embodiments herein disclose a method of turning the natural proteinaceous polymer into a macromonomer.

In addition, the term "co-monomer" refers to monomers that are used to copolymerize with the macromonomer that contains polymerizable unsaturated double bonds.

General Description

Embodiments herein are directed to a new material based on a macromonomer derived from natural proteinaceous polymer. The chemistry based on modifying the functional groups in proteinaceous substrates, as described herein, is more efficient and versatile than methods, such as, for example, those based on the modification of hydroxyl groups in polysaccharides. Thus, as a result of the teachings herein, the novel superabsorbent material prepared by the macromonomer approach herein provides for surprisingly superior properties than provided by conventional methods, such as, but not limited to, free radical grafting copolymerization, and addresses a need highly desired in the field of absorbent and superabsorbent polymer materials.

Accordingly, the novel embodiments and methods disclosed herein form the basis of the present invention. As an exemplary embodiment, introducing polymerizable unsaturated groups onto a natural polymer or its derivative yields a macromonomer. The macromonomer in particular is formed by covalently binding unsaturated carbon-carbon double bonds to a proteinaceous substrate through a reaction of a selected chemical compound and the amino groups on the proteinaceous substrate. The macromonomer is then copolymerized with unsaturated co-monomer(s) to form a crosslinked superabsorbent material.

Specific Description

Turning now to the drawing, FIG. 1 shows an example preparation methodology of a cross-linked polymer network 12 that is the basis of the superabsorbent material of the present application. The network 12 is formed by polymerizing 22 (as also generally denoted with the directional arrow) one or more co-monomer(s) 20 in the presence of the natural polymer-derived macromonomer 10, wherein the natural polymer-derived macromonomer 10 is initially derived from a natural proteinaceous polymer of which often includes a natural polymer backbone 14, amino groups (e.g., denoted as $NH_2$ in FIG. 1) and one or more polymerizable units 18, e.g., units having polymerizable unsaturated double bonds.

In particular, the natural polymer-derived macromonomer 10 is prepared, by introducing polymerizable unsaturated cross-linkable units 18 onto the natural polymer backbone 14 so as to modify the natural polymer itself by the reaction through amino groups with predetermined chemical compounds. For example, suitable chemicals to introduce such cross-linkable units 18 to the macromonomers include, but are not limited to, methacrylic anhydride, itaconic anhydride, glycidyl methacrylate and maleic anhydride. As an example alternative, the natural polymer is pretreated before turned into the macromonomer 10, e.g., the natural polymer is hydrolyzed. The natural polymer-derived macromonomer product can then be used directly in aqueous solution or be used after proper methods of drying.

A hydrogel composition is thus generally formed between a first polymer that is a natural polymer-derived macromonomer 10 and a second polymer formed after the completion of the polymerization, where the natural polymer derivative provides the crosslinkable unit to yield a cross-linked structure that can absorb and retain a significant amount of water.

In some embodiments, the hydrogel composition can be configured via the cross-linked structure of the natural proteinaceous polymer-derived macromonomer 10, a polymerized polymer from the starting co-monomer, and optionally a synthetic polymer. Additionally, extra crosslinking can also be introduced to the hydrogel composition of the present invention by means of adding crosslinking agents to alter the properties of the product. Such crosslinking agents include, but are not limited to, N,N'-methylenebisacrylamide and glutaraldehyde.

With respect to the degradable aspect of the embodiments herein, the beneficially formed hydrogels undergo degradation over time by the degradation of at least some of the cross-linked units, as well as the degradation of the natural polymer proportion. Suitable degradable linkages include, for example, ester, amide and peptide bonds. It is possible to control the degradation rate to the hydrogel by varying the composition of the components and the type and proportion of the cross-linked units, some of which are disclosed above. The choice of components and cross-link methods can also be used to adjust the mechanical properties of the hydrogel.

It is to be appreciated that the formed hydrogels that make up the cross-linked network 12 are often characterized as absorbent or superabsorbent materials depending on the composition and condition of preparation, as disclosed herein. For example, the types of natural polymers that can be used in the absorbent or superabsorbent hydrogel composition of the present invention include natural polymers, such as, for example, proteinaceous polymers. Such natural protein polymers suitable for use herein include, for example, plant proteins such as soy protein, wheat protein, maize proteins, cotton seed protein, fish proteins, and animal proteins such as gelatin and collagen.

In an example embodiment, the hydrolysate of the natural proteinaceous polymer is separated into different fractions based on molecular size/weight and at least one of the fractions is selected to be used in the preparation of the bio-based superabsorbent material. Such separation can be done, for example, by using a membrane or by precipitation in selected solvent. In another example embodiment, the hydrolysate of the natural proteinaceous polymer is separated into different fractions based on solubility in aqueous medium and at least one of the fractions is selected to be used in the preparation of the bio-based superabsorbent material. In another example, embodiment the hydrolysate is separated based on both molecular size/weight and the solubility. Optionally, the separation based on molecular size/weight and/or solubility can be performed after the hydrolysates have been converted into macromonomers.

Superabsorbent polymer compositions of the present invention also can include combinations of any two or more of the foregoing types of natural polymers. Both the natural protein polymers and natural non-protein polymers of the invention may be provided with cross-linkable units, by means known to those of ordinary skill in the art. The non-protein portion of the natural proteinaceous polymer can simply be part of the network. Alternatively, the non-protein portion of the natural proteinaceous polymer may be covalently bound to the network. The protein portion of the natural proteinaceous polymer can optionally be further crosslinked using a crosslinking agent. In one example non-limiting example embodiment, the crosslinking agent used to covalently bind at least part of the protein portion is glutaraldehyde (GA).

It is also to be appreciated that radical initiation to provide more bonding sites on the natural protein can also be implemented when desired. The radical initiation can be done by methods that include, but are not strictly limited to, thermal, redox, UV, microwave and other irradiation. Alternatively, the preparation of hydrogel can be carried out by other polymerization techniques, e.g. ionic polymerization, instead of free radical polymerization, or combination of several techniques.

The polymer chains polymerized from the co-monomer(s) 20 during the synthesis of the superabsorbent hydrogel can also be further cross-linked by adding a crosslinking agent that contains at least two unsaturated carbon-carbon double bonds prior to the final step of producing the superabsorbent polymer. As an example agent, the crosslinking agent used to crosslink the polymer chains polymerized from the co-monomer(s) is N,N'-methylenebisacrylamide (NMBA).

In addition, the types of co-monomers that are suitable for use in the present invention may include monomers that are derived from petroleum-based chemical sources and monomers that are derived from renewable bio-based chemical sources. Suitable co-monomers include acrylic acid and its derivative, acrylamide, methacrylic acid, vinyl amine, N-vinylpyrrolidone, hydroxyethylmethacrylate (HEMA).

Example synthetic polymers, such as, but not limited to, polyvinyl alcohol, can be included in the hydrogel composition based on the capability of imparting desirable mechanical properties and other properties that are deemed beneficial. Generally, the synthetic polymers can be cross-linked onto the network or can be present as a separate component.

As an example method of making the example cross-linked absorbent or superabsorbent hydrogel composition networks 12, a first solution is prepared of a natural polymer macromonomer, with a plurality of cross-linkable units, with at least some degradable units present between the polymer backbone and the cross-linkable units, and a second solution is prepared of one or more co-monomer(s) and/or derivatives, having polymerizable unsaturated units. The two solutions are then mixed and the reaction is initiated to form a cross-linked hydrogel.

Another example method of making the superabsorbent material often includes a step of hydrolyzing the natural proteinaceous polymer that contains at least one protein and then converting the hydrolysate to a macromonomer that contains polymerizable unsaturated double bond through a reaction between a suitable double bond-containing chemical compound and the amino group in the hydrolysate. The derived macromonomer is thereafter co-polymerized with one or more co-monomer(s) to produce a crosslinked polymer that is a superabsorbent material, with or without the use of additional crosslinking agent(s).

It is to be appreciated that the cross-link units in the superabsorbent polymer product can be gradually hydrolyzed over time, resulting in the beneficial breakdown of the hydrogel. The natural polymer part of the hydrogel eventually breaks down as well. It is recognized that the rate of degradation is determined at least in part by the type of cross-link unit, as well as the proportion of the natural polymer in the hydrogel product. A shortened or prolonged time period of breakdown may be desired according to the particular application.

As an alternative example application embodiment, the superabsorbent polymer is surrounded by another material. Such a configuration can thus form sanitary products for absorbing body fluids including, but not strictly limited to, a baby diaper, an adult incontinence product, and a feminine hygiene product. As alternative beneficial applications, the superabsorbent polymers provided herein can be used alone or together with other materials and/or chemical compounds to make a product for soil water retention and controlled release of nutrients, pesticides, insecticides and other chemicals for the control of plant growth. As an addition alternative example application, the superabsorbent polymer disclosed herein can be used alone or together with other materials and/or chemical compounds for a myriad of industrial applications.

The present invention will be more fully understood by reference to the following examples, which are intended to be illustrative of the present invention, but not limiting thereof.

EXAMPLES

Measurement of Swelling

The swelling of the superabsorbent polymer materials is evaluated by comparing the weight of the swollen gel to that of the dry gel and denoted as Q. The swelling ratio based on weight, Q, is determined according to the following formula:

$$Q=(m_s-m_d)/m_d,$$

wherein the subscripts s and d refers to the swollen state and the dry state of the gel respectively. The weight-based swelling ratio, q, when the swelling equilibrium is reached is denoted $Q_e$. The measurement is done by separating the swollen gel and the excess water using a device such as a tea bag, or any other device that has suitable mesh size to allow water to pass and prevent gel particles from passing through. The unbound water was removed using a paper towel. The measurement of swelling can be done in aqueous solutions with varying ionic strength and pH, at different temperature, under pressure or other conditions a value of the swelling ratio is desired to be known. Unless otherwise mentioned, the swelling ratio value refers to that measured in distilled water at room temperature essentially free of pressure or stress.

Example 1

A hydrolysate of soy protein isolate with protein content greater than about 85% is obtained by sodium hydroxide hydrolysis of the SPI. The hydrolysate remains in the solution and is used immediately thereafter to produce the macromonomer. The hydrolysate is reacted with methacrylic anhydride so as to bind polymerizable double bonds to the protein molecular structure, as illustrated in FIG. 1. The macromonomer is used again immediately after the modification to produce the superabsorbent hydrogel. The time needed to complete the reaction is typically between a range from about 10 minutes up to about 60 min. The reaction is often carried out at room temperature. It is not necessary to separate the modified hydrolysate from the by-product of modification, which is methacrylic acid in the example. The mixture is used directly to produce the hydrogel. In the last step, hydrogel is prepared by mixing the macromonomer, the co-monomer(s) and the initiators and followed by carrying out the reaction at 40° C. for about 1 hour. Potassium persulfate (KPS) and sodium bisulfite (SBS) is used as the initiating system. Stirring is provided at the initial 1 to about 2 minute time frame to ensure homogenization of the mixture and then stopped and the mixture is allowed to cure 40° C. for the rest of reaction time. The hydrogel is formed using water as a solvent.

Example 2

Comparison of equilibrium swelling ratio, $Q_e$, of superabsorbents prepared with hydrolysates having different degree of hydrolysis. Table 1, as shown below, lists superabsorbent polymer compositions prepared under different hydrolysis conditions of the SPI. During hydrolysis, the SPI to water weight ratio is about 1 up to about 6.5. The degree of hydrolysis of the hydrolysates is controlled by varying the NaOH to SPI weight ratio in the reaction medium prior to the hydrolysis step. The hydrolysis reaction is carried out at about 70° C. for up to about 2 hours. The methacrylic anhydride that is used to modify the SPI is 2 wt. % to SPI. The pH of the reaction media just prior to polymerization is kept the same at about 7.0 up to about 7.6. The weight to volume ratio (w/v) of the reactants in water is about 1/6 (w/v). KPS is used at a level of about 2.5 wt. % to monomer (AA), and SBS to KPS weight ratio is about 1/2. The polymerization reaction is carried out at about 40° C. for up to about 1 hour. The weight ratio between the natural polymer and the co-monomer is about 1 to 1 (i.e., 50% natural polymer in the composition of the solid).

TABLE 1

| NaOH/SPI (wt. %) | $Q_e$ (g/g) |
| --- | --- |
| 5% | 110 |
| 6% | 153 |
| 7% | 193 |
| 8% | 241 |

The table above shows the profound effect that the degree of hydrolysis has on the equilibrium swelling capacity of the example prepared superabsorbent hydrogels.

Example 3

The interplay of the effect of hydrolysis of SPI and the amount of MAh used are shown in Table 2 below. During hydrolysis the SPI to water weight ratio was 1 to 8. The NaOH to SPI weight ratio in the reaction medium was varied from 5.5~7.5% prior to the hydrolysis step. The hydrolysis reaction was carried out at 60° C. for 2 hr. The amount of methacrylic anhydride used to modify the SPI was varied from 0.67 to 2 wt. % to SPI. The pH of the reaction media just prior to polymerization was kept the same at 7.0~7.6. The weight to volume ratio of the reactants in water was 1/7.5 (w/v). KPS was used at a level of 2.5 wt. % to monomer (AA), and SBS to KPS weight ratio was 1/1.3. The polymerization reaction was carried out at 40° C. for 1 hr. The weight ratio between the natural polymer and the co-monomer was 1 to 1 (i.e. 50% natural polymer in the composition of the solid).

TABLE 2

| NaOH/SPI (wt. %) | MAh/SPI (wt. %) | $Q_e$ (g/g) |
| --- | --- | --- |
| 5.5% | 0.67 | 154 |
| 5.5% | 1.33 | 135 |
| 6.5% | 0.67 | 122 |
| 6.5% | 1.33 | 132 |

TABLE 2-continued

| NaOH/SPI (wt. %) | MAh/SPI (wt. %) | $Q_e$ (g/g) |
|---|---|---|
| 6.5% | 2.0 | 108 |
| 7.5% | 0.67 | 89 |

Table 2 above shows that under the conditions of the experiments in this example, at lower degree of hydrolysis, a lower amount of MAh results in higher equilibrium swelling. At higher degree of hydrolysis, it appears that too low a content of MAh, hence double bonds in the macromonomer, results in a lower equilibrium swelling ratio, where the optimal swelling ratio shows at an intermediate amount of MAh.

Example 4

During hydrolysis the SPI to water weight ratio was 1 to 6.5. The NaOH to SPI weight ratio was either 6% or 8% prior to the hydrolysis step. The hydrolysis reaction was carried out at 70° C. for 2 hr. The amount of methacrylic anhydride (MAh) used to modify the SPI was varied from 2 to 4 wt. % to SPI. The pH of the SPI hydrolysate solution was not changed, i.e., as-is after the hydrolysis, prior to the functionalization.

The contents of free amino group in SPI hydrolysate and functionalized SPI were determined by OPA method with a UV-vis spectrometer. Briefly, o-phthaldialdehyde (OPA) reagent was prepared and mixed with SPI hydrolysate or functionalized SPI solution with known sample concentration. Absorbency at ca. 335 nm was read after the mixture was allowed to stand for two minutes. Samples of SPI hydrolysate and functionalized SPI were prepared by directly freeze-drying the solution after hydrolysis or functionalization. The content of amino groups per gram sample can be calculated, using an amino acid, serine, as a standard, as follows:

$$[-NH_2] = \frac{A_{SP}}{conc._{SP}} \cdot \frac{conc._{Se}}{A_{Se}} \cdot \frac{1000 \text{ mmol/mol}}{105.09 \text{ g/mol}},$$

where the subscripts SP and Se stands for soy protein sample, i.e., the SPI hydrolysate or functionalized SPI, and serine standard, respectively, and A is the absorbency at ca. 335 nm, conc. is the concentration of soy protein sample or the serine standard in solutions, 105.09 is the molar mass of serine. Average value of absorption from three replicates was used to calculate the amino group content for each sample. The absorbency of serine standard at a concentration of 0.3 g/L was 2.1564 mmol/g. The conc. of SP samples in this experiment was 6 g/L.

The characterizations of MAh-functionalized SPI hydrolysates at a degree of hydrolysis controlled by the NaOH/SPI weight ratio of 6% are shown in Table 3 below. The sample code, x %-y %, denotes the NaOH/SPI weight ratio (x %) and the MAh/SPI weight ratio (y %). The vinyl content is calculated from the reduction in amino group content per gram sample. The degree of modification is the ratio between the vinyl groups in the functionalized sample and the amino groups in the original hydrolysate sample with same degree of hydrolysis. The efficiency of the functionalization reaction is calculated based on the vinyl group grafted to the soy protein sample and the amount of MAh used. The results shown in Table 3 shows about 50% of amino groups in the SPI hydrolysates is substituted by the vinyl group from MAh at an MAh/SPI weight ratio of 4%, and the vinyl group content is about 0.176 mmol/g sample at this particular combination of levels of hydrolysis and functionalization.

TABLE 3

| Sample code | MAh/SPI (wt. %) | [—NH$_2$] (mmol/g) | Vinyl content (mmol/g) | Degree of modification (%) | Efficiency (%) |
|---|---|---|---|---|---|
| 6%–0% | 0 | 0.351 | 0 | 0 | n.a. |
| 6%–2% | 2 | 0.257 | 0.094 | 26.8 | 72.5 |
| 6%–3% | 3 | 0.208 | 0.143 | 40.7 | 73.4 |
| 6%–4% | 4 | 0.175 | 0.176 | 50.1 | 67.7 |

Table 3 above shows that under the conditions of the experiments in this example, with NaOH/SPI weight ratio being 6% prior to the hydrolysis, a higher weight ratio of MAh/SPI results in higher degree of modification of the amino groups in the SPI hydrolysates.

The characterizations of MAh-functionalized SPI hydrolysates at a degree of hydrolysis controlled by the NaOH/SPI weight ratio of 8% are shown in Table 4 below. Comparing results shown in Table 4 to those shown in Table 3, it can be seen that, at different degrees of hydrolysis controlled by the NaOH/SPI weight ratio, the vinyl contents in the functionalized SPI hydrolysate samples are somewhat different even if the MAh/SPI weight ratios are the same. This is because the reaction efficiencies of the modification are different for the two groups of SPI hydrolysates. Generally, the efficiency of the functionalization of amino groups in SPI hydrolysates by MAh in aqueous solutions is high, ranging from 50%~70% under the conditions of the experiments in this example.

TABLE 4

| Sample code | MAh/SPI (wt. %) | [—NH$_2$] (mmol/g) | Vinyl content (mmol/g) | Degree of modification (%) | Efficiency (%) |
|---|---|---|---|---|---|
| 8%–0% | 0 | 0.395 | 0 | 0 | n.a. |
| 8%–2% | 2 | 0.335 | 0.060 | 15.2 | 46.2 |
| 8%–3% | 3 | 0.304 | 0.091 | 23.0 | 46.8 |
| 8%–4% | 4 | 0.267 | 0.128 | 32.4 | 49.3 |

Table 4 above shows that under the conditions of the experiments in this example, with NaOH/SPI weight ratio being 8% prior to the hydrolysis, a higher weight ratio of MAh/SPI results in higher degree of modification of the amino groups in the SPI hydrolysates.

Example 5

A hydrolysate of soy protein isolate (SPI) is obtained by hydrolysis of the SPI using sodium hydroxide (NaOH). During hydrolysis, the SPI to water weight ratio is about 6.5. The NaOH to SPI weight ratio is about 8% in the reaction medium prior to the hydrolysis step. The hydrolysis reaction is carried out at about 70° C. for about 2 hours. The methacrylic anhydride (MAh) that is used to modify the SPI is 3 wt. % to SPI. The functionalization reaction is carried out at room temperature for 30 min. The aqueous mixture containing modified SPI is used directly in the next step to produce the hydrogel. Hydrogel is prepared by mixing the functionalized SPI macromonomer, the co-monomers and the initiators and followed by carrying out the reaction at 85° C. for about 1 hour. The weight ratio between the natural polymer and the co-monomers is about 1 to 1 (i.e., 50% natural polymer in the composition of the solid). Acrylamide (AAm) and acrylic acid (AA) are used together as the co-monomers at a weight ratio of AAm to AA of 1 to 3. About 0.55 g NaOH is used per gram of AA to neutralize the AA so that the pH of the reaction medium is adjusted to 7.0 prior to the polymerization. Potassium persulfate (KPS) and sodium bisulfite (SBS) is used as the initiating system. KPS is used at a level of about 1.25 wt. % to the total amount of co-monomers, and SBS to KPS weight ratio is about 1/2. Stirring is provided at the initial 1 to about 2 minute time frame to ensure homogenization of the mixture and then stopped and the mixture is allowed to cure 85° C. for the rest of reaction time. The hydrogel formed is dried and the equilibrium swelling ratio, $Q_e$, in distilled water is measured to be about 62 g/g.

Example 6

A hydrolysate of soy protein isolate (SPI) is obtained by hydrolysis of the SPI using potassium hydroxide (KOH). 1.33 g SPI is used in this example. During hydrolysis, the SPI to water weight ratio is about 6.5. The KOH to SPI weight ratio is about 9% in the reaction medium prior to the hydrolysis step. The hydrolysis reaction is carried out at about 70° C. for about 1.5 hours. The methacrylic anhydride (MAh) that is used to modify the SPI is 10 wt. % to SPI. The functionalization reaction is carried out at room temperature for 30 min. The aqueous mixture containing modified SPI is used directly in the next step to produce the hydrogel. Hydrogel is prepared by mixing the functionalized SPI macromonomer, the co-monomer and the initiators. Acrylamide (AAm) is used as the co-monomer. The weight ratio between the natural polymer and the co-monomer is about 1 to 3 (i.e., 25% natural polymer in the composition of the solid). 4 g AAm is dissolved in 10 ml $H_2O$. The solution is mixed with the functionalized SPI macromonomer after 30 min of functionalization reaction. 100 mg potassium persulfate (KPS) and 30 mg sodium bisulfite (SBS) are added to the mixture. Stirring is provided for homogenization of the mixture. Within 5 min of addition of the initiator pair at room temperature, gelation occurs. A firm gel containing approximately 25 wt. % SPI and 75 wt. % polyacrylamide is formed. The hydrogel formed is dewatered using acetone.

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

The invention claimed is:

1. A crosslinked superabsorbent polymer material comprising:
    a proteinaceous plant-based natural polymer substrate comprising a plurality of protein molecules wherein at least part of the protein molecules are modified at amino groups of the protein molecules with one or more polymerizable group-bearing compounds; and
    polymers which are different from said protein molecules and which are formed from one or more monomers or co-monomers, wherein said polymers are covalently bonded to said one or more polymerizable group-bearing compounds, and at least some of said plurality of protein molecules are bonded together by said polymers forming a covalently crosslinked proteinaceous plant-based natural polymer substrate,
    wherein said covalently crosslinked proteinaceous plant-based natural polymer substrate is capable of absorbing and retaining water at 10 to 1000 times a weight of said covalently crosslinked proteinaceous plant-based natural polymer substrate.

2. The crosslinked superabsorbent polymer material according to claim 1, wherein the at least one of said one or more polymerizable group-bearing compounds is selected from the group consisting of methacrylic anhydride, itaconic anhydride, glycidyl methacrylate, and maleic anhydride.

3. The crosslinked polymer material of claim 1 wherein the proteinaceous plant-based natural polymer substrate is selected from the group consisting of soy protein, hemp seed protein, cotton seed protein, and pea protein.

4. The crosslinked superabsorbent polymer material according to claim 1, wherein the crosslinked superabsorbent polymer material is biodegradable.

5. The crosslinked superabsorbent polymer material according to claim 1, wherein the covalently crosslinked proteinaceous plant-based natural polymer substrate is configured with desired materials to produce a sanitary product.

6. The crosslinked superabsorbent polymer material according to claim 1, wherein the covalently crosslinked proteinaceous plant-based natural polymer substrate is configured with desired materials to produce a diaper.

7. The crosslinked superabsorbent polymer material according to claim 1, wherein the covalently crosslinked proteinaceous plant-based natural polymer substrate is configured with a desired material to produce an article selected from the group consisting of a sanitary product, a diaper, a water treatment product, a water retaining coating around a seed, a soil water retention product, a pesticide controlled release material, and a fertilizer controlled release vehicle.

8. The crosslinked superabsorbent polymer material according to claim 1, wherein at least one of the one or more monomers or co-monomers is selected from the group consisting of acrylic acid, methacrylic acid, acrylamide, vinyl amine, N-vinylpyrrolidone, and hydroxyethylmethacrylate.

* * * * *